(12) United States Patent
Adaway et al.

(10) Patent No.: US 7,102,042 B2
(45) Date of Patent: Sep. 5, 2006

(54) METHOD FOR PRODUCING SUBSTITUTED FLUORENE MONOMERS

(75) Inventors: Timothy J. Adaway, Midland, MI (US); Michael A. Gonzalez, Sanford, MI (US); Weishi Wu, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 572 days.

(21) Appl. No.: 10/325,287

(22) Filed: Dec. 19, 2002

(65) Prior Publication Data

US 2004/0122266 A1 Jun. 24, 2004

(51) Int. Cl.
*C07C 25/18* (2006.01)
*C07C 25/22* (2006.01)
*C07C 25/24* (2006.01)

(52) U.S. Cl. ............... 570/247; 570/206; 570/190; 570/216; 570/246; 570/252; 570/253; 570/257; 570/261

(58) Field of Classification Search ........... 570/247, 570/206, 190, 216, 246, 252, 253, 257, 261
See application file for complete search history.

(56) References Cited

PUBLICATIONS

Bulletin L'Academie Polonaise Des Sciences, Makosza, 1967, 15, pp. 165–167.

*Primary Examiner*—Elvis O. Price
(74) *Attorney, Agent, or Firm*—Susan Moeller Zerull

(57) ABSTRACT

A method for preparing a composition of the formula

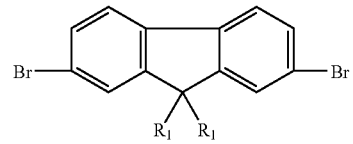

in a yield greater than 50% where $R^1$ is C 1–20 comprising the steps of combining fluorene or dibromo flourene, an excess of alkali metal hydroxide and a halogenated alkyl in the presence of a phase transfer catalyst but in the absence of a polar aprotic solvent; heating the combination; and separating the dialkylated fluorene or dialylated dibromo fluorene. If the flourene is not brominated prior to alkylation, the dialkylated fluorene is then brominated.

9 Claims, No Drawings

METHOD FOR PRODUCING SUBSTITUTED FLUORENE MONOMERS

FIELD OF INVENTION

This invention relates to a novel method of producing 2,7-dibromo-9,9-dialkyl fluorene monomers.

BACKGROUND OF INVENTION 9,9-disubstituted,2,7-dibromo fluorenes are useful starting materials for numerous polymers including polymeric light emitting diodes. Bromination at the 2 and 7 position creates sites for polymerization of the fluorene monomer. Dialkylation at the 9 positions advantageously increases solubility for creation of polymer films.

The use of alkali metal hydroxides in the dialkylation of fluorene is reported. However, in most reports polar aprotic solvents are also used. Additionally, only bromoalkanes are used as the alkylating-agent.

Alkylation of fluorene without a polar aprotic solvent in the presence of aqueous (50%) sodium hydroxide and the phase transfer catalyst triethyl benzylammonium chloride at temperatures of 90 to 100 degrees C. is reported in Makosza, Bulletin L'Academie Polonaise Des Sciences, 1967, 15 165–67. However, the reported reaction produced a mixture of 9-butylfluorene and 9,9-dibutylfluroene. The percentage yield is not indicated. Makosza then states that "[b]etter results were obtained when a small amount of dimethylsulphoxide (DMSO) was added." Id at 166. The result using DMSO yielded a 65% mixture of 9,9 -dibutylfluorene and 9-butylfluorne. Id. at 167.

Additionally, dibromo dialkyl fluorene has been produced through alkylation of 2,7-dibromo fluorene. However, the 9,9-alkylation conducted via that route also required use of a polar aprotic solvent.

Use of a polar aprotic solvent and other solvents present disadvantages relating to waste disposal requirements and disposal costs.

A process to produce high yields of dibromo dialkyl fluorene using alkali metal hydroxide without the use of polar aprotic solvents would be beneficial. Additionally, a method of alkylation which could use a variety of haloalkanes, especially chloralkanes, would also be desirable.

SUMMARY OF INVENTION

In one aspect the invention is a method for preparing a composition of the formula

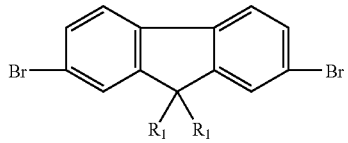

in a yield greater than 50% where $R_1$ is an alkyl or substituted alkyl of 1 to 20 carbon atoms comprising the steps of combining fluorene or dibromo flourene, an excess of alkali metal hydroxide and a halogenated alkyl in the presence of a phase transfer catalyst but in the absence of a polar aprotic solvent; heating the combination; and separating the dialkylated fluorene or dialylated dibromo fluorene. If the flourene is not brominated prior to alkylation, the dialkylated fluorene is then brominated.

The processes of this invention are advantageous because they can be run without polar aprotic solvents. The processes provide improved products yields. Surprisingly, the processes allow for use of chloralkanes as alkalyating agents. Use of chloroalkanes provides ease in waste handling and recycling of reaction materials. The processes can also be run at a range of temperatures.

DETAILED DESCRIPTION

The process for alkylation of fluorene is performed in the presence of an aqueous alkali metal hydroxide. Preferred alkali metal hydroxides are sodium hydroxide and potassium hydroxide. Sodium hydroxide is most preferred. The amount of alkali metal hydroxide is used in sufficient excess to facilitate the efficient reaction of an alkyl halide and fluorene. Preferably, five equivalents or greater of alkali metal hydroxide are used in relation to fluorene, and more preferably fifteen equivalents or greater of alkali metal hydroxide are used.

The alkylation reaction can be run at any temperature from room temperature to 80° C. Most preferably the reaction is heated and run at about 40 to 50° C.

The organic and aqueous phases of the reaction are separated by washing techniques known to those skilled in the art. When the reaction mixture is allowed to phase separate, the NaCl by-product largely remains suspended in the organic phase. The resulting aqueous phase contains the excess NaOH in a form convenient for recycle.

The organic phase is washed with water or filtered to remove the NaCl by-product. The resulting organic phase is suitable to be used in the ensuing bromination without further purification.

Bromination is carried out by standard techniques known in the literature. Possible brominating agents include bromine, N-bromosuccinimide (NBS) or 1,3-dibromo-5,5-dimethylhydantoin. The brominating agent is added in an amount sufficient to brominate the dialkyl flourene at both the 2 and 7 carbon positions.

Additionally, 2,7-dibromofluorene can also be alkylated with an alkali metal hydroxide, phase transfer catalyst, and a haloalkane without a polar aprotic solvent. This process also provides a high yield. The alkylation yield is greater than 75%.

Regardless of whether the flourene is brominated before or after alkylation, the process surprisingly allows alkylation using chloroalkanes as well as bromo and iodo alkanes.

The alkylation process is an interfacial process. A phase transfer catalyst is used. Selection of a specific phase transfer catalyst eliminates the need for polar aprotic solvents. The phase transfer catalyst may be a tetra alkyl amonium or phosphonium cation bonded to four alkyl groups which in total contain at least sixteen carbon atoms but of which no more than one of the alkyl groups is a methyl group. The phase transfer catalyst will also include an anion selected from the group consisting of $Cl^-$, $Br^-$, $I^-$, $HSO_4^-$, $HCO_3^-$ or $OH^-$. Preferred phase transfer catalysts include: tetra alkyl ammonium chlorides, trialkyl methyl ammonium chlorides, tetra alkyl ammonium bromides, triaklyl methyl ammonium bromides, tetra alkyl ammonium iodides, trialkyl methyl ammonium iodides, tetra alkyl ammonium hydroxides, trialkyl methyl ammonium hydroxides, tetra alkyl phosphonium chlorides, tetra alkyl phosphonium bromides, tetra alkyl phosphonuim iodides, and tetra alkyl phosphonium hydroxides. The more preferred phase transfer catalysts are compounds of the formulas $(C_8H_{17})_4N^+X^-$, $(C_4H_9)_4N^+X^-$, and $(C_{8-10})_3N^+CH_3X^-$ wherein $X^-$ is a halogen ion. The phase transfer catalysts preferably are used in an amount of 0.01 mole or greater per mole of fluorene, more preferably 0.025 per mole or greater per mole of fluorene and most preferably 0.05 per mole or greater per mole of fluorene.

A variety of alkylhalides may be used as alkylating agents. Surprisingly, chlorinated alkanes are efficient and effective dialkylating agents in the process. Alkylhalides that can be used include alkyl halides with carbon chains of 1 to 20. Preferably the length of the carbon chain is greater than three and less than nine. The halogen in the alkyl halide preferably is iodine, chlorine, or bromine. The alkyl halide may be primary, benzylic, or allylic. The alkyl chains can be substituted with a variety of groups that are inert towards the alkylation process (i.e. aryl or alkylenyl). Chloroalkanes are most preferable. The alykyhalide is contacted with the fluorene or dibromofluorene in a mole ratio such that a high yield of 9,9-dialkylfluorene or 2,7-dihalo-9,9-dialkyl fluorene is prepared. Preferably the mole ratio of alkyl halide to fluorene or dibromofluorene is 2:1 or greater, more preferably 2.1:1 or greater and even more preferably 2.2:1 or greater.

EXAMPLES

The following examples are included for illustrative purposes only. The examples do not limit the scope of the claims. Unless otherwise stated, all parts and percentages are by weight.

Example 1a

Preparation of 9,9-di-n-hexylfluorene

A 250 ml flask was equipped with an electric stirrer, thermowell, and nitrogen pad. It was loaded at room temperature with 24.9 g (0.15 moles) fluorene, 39.5 g (0.327 moles) chlorohexane, 2.9 g of tricaprylylmethylammonium chloride (0.007 moles), and 180 g (2.25 moles) 50% NaOH. No exotherm is observed. It was then heated at 50° C. until reaching 99+% conversion. The reaction took approximately 12 hours. While maintaining at 50° C., the liquid phases were separated (the solid NaCl remained suspended in the top organic phase). The organic phase was extracted with 1×50 ml water followed by 1×25 ml 3.5% HCl (acid wash caused color change from dark to orange). The resulting organic phase weighed 55.8 g and had an area percentage GC analysis for dialkylated product in the 90's. The crude product was forwarded directly to the bromination reaction step. Based on the accountability in the bromination, the yield of the PTC alkylation was 92+%.

Example 1b

Preparation of 2,7-dibromo-9,9-di-n-hexyl fluorene (with NBS)

A 250 ml flask equipped with a electric stirrer, nitrogen pad, thermowell, and heating mantle was wrapped in foil to minimize the introduction of light. It was loaded with 17.0 g (≦0.047 moles) crude 9,9-di-n-hexylfluorene from Example 1a, 21.1 g (0.119 moles) of N-bromosuccinimide (NBS), and 53.2 g of water. The system was heated to 55° C. for 19 hours where the conversion was determined to be 98.2% (by area % GC). Addition of 1.8 g (0.017 moles) NaHSO$_3$ caused the color to change from red to yellow. The temperature was then increased to 65° C. The phases were separated. The top aqueous phase was extracted with 1×8 g of toluene. The combined organic phases were mixed with 32 g of acetonitrile and heated to reflux. It was then cooled to 10° C. and filtered. Air-Drying yielded 19.9 g of a yellow solid, an 84.3% isolated yield (based on fluorene). Analyzing the filtrate gave a total accountability based on fluorene of about 92%.

Example 2a

Preparation of 9,9-di-n-octylfluorene

The reaction was run in a 250 ml flask equipped with an electric stirrer, thermowell, and nitrogen pad. It was loaded at room temperature with 25 g (0.15 moles) fluorene, 49 g (0.327 moles) 1-chlorooactane, 2.9 g of tricaprylylmethylammonium chloride (0.007 moles), and 163.4 g (2.25 moles) 55% NaOH. No exotherm was observed. It was heated at 50° C. until reaching 99+% conversion, approximately 23 hours. While maintaining at 50° C., 80 ml of water was added. The organic phase was extracted with 1×50 ml 3.5% HCl (acid wash caused color change from dark to orange). The resulting organic phase weighed 65.4 g and had an area % GC analysis for the dialkylated product of 87%. The crude was directly forwarded to the bromination reaction. Based on the yield of the bromination step, the yield in the PTC alkylation was over 86%.

Example 2b

Preparation of 9,9 dioctyl dibromofluorene (with NBS)

A 250 ml flask equipped with an electric stirrer, nitrogen pad, thermowell, and heating mantle was wrapped in foil to minimize the introduction of light. It is loaded with 21.5 g (≦0.049 moles) crude 9,9 dioctyl fluorene from example 2a, 23 g (0.129 moles) of N-bromosuccinimide (NBS), and 53.3 g of water. The system was heated to 60° C. for 23 hours. The addition of 2 g (0.019 moles) NaHSO$_3$ caused the color to change from red to yellow. The temperature was increased to 65° C. The phases were separated, giving 28.3 g of (bottom) oil phase. The aqueous phase was extracted with 1×10 g of toluene. The combined organic phases were mixed with 40 g of acetonitrile and heated to reflux, forming two liquid phases. The heated phases were cooled, seeded around 50° C., further cooled to 18° C., and filtered. The air-dried cake gave 25.3 g of tan solid for a yield of 86% (based on fluorene).

Example 3

Alkylation of 2,7 dibromofluorene

A mixture of 16.2 g (0.05 moles) dibromofluorene, 13.7 g (0.113 moles) chlorohexane, 0.9 g (0.002 moles) tricaprylmethylammonium chloride (commercially known as Aliquat 336) and 15 ml of toluene was heated to 55° C. under nitrogen. To this was shot added 60.1 g (0.76 moles) 50% NaOH. No exotherm was detected. The system was heated at 55° C. for 3 hours, 65° C. for 19.5 hours, then 75° C. for 11 hours. At this point, a GC analysis indicated 98+% conversion. The system was cooled to 60° C. The solids (NaCl) remained suspended in the top organic phase. The aqueous phase was separated and the organic phase was extracted with 1×18 ml water, keeping the system at about 60° C. This seemed to be enough water to dissolve all of the solids. The organic phase remained the top phase. The aqueous phase was separated and the organic phase extracted with 19 ml 3.5% HCl. The organic phase now became the bottom phase and changed color from dark to green and then orange. The organic phase was separated off and product precipitated with of 30.6 g of acetonitrile. It was cooled to 10° C. and filtered. The cake was rinsed with 1×10 ml of acetonitrile and air-dried to 19.3 g of a pale yellow solid. By area % GC it was 98.3% 2,7-dibromo-9,9-di-n-hexylfluorene, a 77.1% yield.

What is claimed is:

1. A method for preparing a composition of the formula

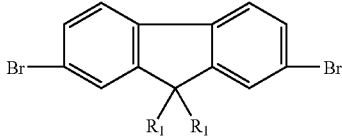

in a yield greater than 50% where $R_1$ is an alkyl or substituted alkyl of 1 to 20 carbon atoms comprising the steps of (1) combining fluorene or dibromo fluorene, an excess of alkali metal hydroxide and a halogenated alkyl or halogenated substituted alkyl in the presence of a phase transfer catalyst but in the absence of a polar aprotic solvent to produce dialkylated fluorene or dialkylated dibromo fluorene; (2) heating the combination; (3) separating the dialkylated fluorene or dialkylated dibromo fluorene, and (4) if fluorene was used in Step 1, reacting the separated dialkylated fluorene with bromine or a brominated compound.

2. The method of claim 1 in which the alkali metal hydroxide is sodium hydroxide or potassium hydroxide.

3. The method of claim 2 in which the alkali metal hydroxide is present from about five to fifteen equivalents.

4. The method of claim 1 in which the combined fluorene, alkyl halide, phase transfer catalyst, and alkali metal hydroxide are heated to between 20° C. and 80° C.

5. The method of claim 1 in which the halogenated alkyl or substituted halogenated alkyl comprises from 1 to 20 carbon atoms.

6. The method of claim 1 in which the halogenated alkyl or substituted alkyl is a chloroalkyl or substituted chloroalkyl.

7. The method of claim 1 wherein the phase transfer catalyst comprises a tetra alkyl ammonium or tetra alkyl phosphonium cation, four alkyl groups which in total contain at least sixteen carbon atoms providing that no more than one of the alkyl groups is a methyl group, and an anion selected from the group consisting of $Cl^-$, $Br^-$, $I^-$, $HSO_4^-$, $HCO_3^-$, or $OH^-$.

8. The method of claim 1 in which the phase transfer catalyst is selected from the group consisting of tetra alkyl ammonium chlorides, trialkyl methyl ammonium chlorides, tetra alkyl ammonium bromides, trialkyl methyl ammonium bromides, tetra alkyl ammonium iodides, trialkyl methyl ammonium iodides, tetra alkyl ammonium hydroxides, trialkyl methyl ammonium hydroxides, tetra alkyl phosphonium chlorides, tetra alkyl phosphonium bromides, tetra alkyl phosphonium iodides, and tetra alkyl phophonium hydroxides.

9. The method of claim 1 in which the phase transfer catalyst is selected from the formulas

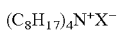

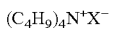

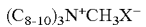

wherein $X^-$ is a halogen ion.

* * * * *